(12) United States Patent
Rajagopalan et al.

(10) Patent No.: US 8,618,820 B2
(45) Date of Patent: Dec. 31, 2013

(54) METHOD AND DEVICE FOR MEASURING THE PURITY OF ULTRAPURE WATER

(75) Inventors: Pascal Rajagopalan, Aulnay-sous-Bois (FR); Antony Vanheghe, Asnieres sur Seine (FR); Celine Le Ninivin, Verneuil sur Seine (FR); Aristotelis Dimitrakopoulos, Saint Martin de Nigelles (FR)

(73) Assignee: EMD Millipore Corporation, Billerica, MA (US)

( * ) Notice: Subject to any disclaimer, the term of this patent is extended or adjusted under 35 U.S.C. 154(b) by 346 days.

(21) Appl. No.: 12/994,208

(22) PCT Filed: Jun. 4, 2009

(86) PCT No.: PCT/IB2009/005849
§ 371 (c)(1),
(2), (4) Date: Nov. 23, 2010

(87) PCT Pub. No.: WO2009/147511
PCT Pub. Date: Dec. 10, 2009

(65) Prior Publication Data
US 2011/0068812 A1      Mar. 24, 2011

(30) Foreign Application Priority Data

Jun. 6, 2008   (FR) ...................................... 08 53785

(51) Int. Cl.
*G01R 27/08*   (2006.01)
(52) U.S. Cl.
USPC .............................. 324/694; 210/93; 324/439
(58) Field of Classification Search
None
See application file for complete search history.

(56) References Cited

U.S. PATENT DOCUMENTS

| 4,691,168 A | 9/1987 | Dzula |
| 5,272,091 A | 12/1993 | Egozy et al. |
| 5,518,608 A | 5/1996 | Chubachi |

(Continued)

FOREIGN PATENT DOCUMENTS

| EP | 0 498 888 A1 | 6/1992 |
| EP | 0 581 157 A1 | 2/1994 |
| WO | 2007/053515 A1 | 5/2007 |

OTHER PUBLICATIONS

Final Rejection mailed Jan. 26, 2012 in co-pending U.S. Appl. No. 12/455,418.

(Continued)

*Primary Examiner* — Arleen M Vazquez
*Assistant Examiner* — Feba Pothen
(74) *Attorney, Agent, or Firm* — Nields, Lemack & Frame, LLC

(57) ABSTRACT

This is a method for analyzing the purity of water at the outlet from a purification device. It includes the following steps: a) sending the liquid at the outlet from the filter means to a resistivity measuring cell to determine its resistivity $\rho_{UPW}$; b) establishing a reference mode by exposing a portion of the liquid to said oxidation means (2) during a given number of significantly different time periods; c) determining by regression the resistivity at infinity $\rho_{\infty REF}$ of said liquid in this reference mode; d) establishing an analysis mode by causing said liquid to be analyzed to pass through the resistivity measuring cell; e) determining the resistivity at infinity $\rho_\infty$ of said liquid in this analysis mode by successive iterations; and f) calculating the quantity of organic compounds contained in the purified liquid from this resistivity at infinity $\rho_\infty$ and at least the values $\rho_{UPW}$ and $\rho_{\infty REF}$.

15 Claims, 2 Drawing Sheets

(56) References Cited

U.S. PATENT DOCUMENTS

| | | | |
|---|---|---|---|
| 5,868,924 A | 2/1999 | Nachtman et al. | |
| 7,057,400 B2* | 6/2006 | Gaignet | 324/696 |
| 8,179,141 B2* | 5/2012 | Rajagopalan et al. | 324/442 |
| 2004/0112829 A1 | 6/2004 | Jenkins et al. | |
| 2005/0165575 A1 | 7/2005 | Mettes | |
| 2009/0319194 A1 | 12/2009 | Rajagopalan et al. | |

OTHER PUBLICATIONS

Advisory Action mailed Apr. 9, 2012 in co-pending U.S. Appl. No. 12/455,418.

Office Action mailed Dec. 5, 2012 in co-pending U.S. Appl. No. 12/455,418.

Office Action mailed Sep. 16, 2011 in corresponding U.S. Appl. No. 12/455,418.

Notice of Allowance mailed May 13, 2013 in co-pending U.S. Appl. No. 12/455,418.

French Search Report dated Jan. 16, 2009.

Light, et al, "The Fundamental Conductivity and Resistivity of Water", Electrochemical and Solid-State Letters, 8 (1), E16-E19 (2005) XP-002511049.

International Search Report dated Oct. 21, 2009.

Co-pending U.S. Appl. No. 13/914,880, filed Jun. 11, 2013; Inventors Pascal Rajagopalan, Antony Vanheghe, Celine Le Ninivin Glipa, Aristotelis Dimitrakopoulos.

* cited by examiner

METHOD AND DEVICE FOR MEASURING THE PURITY OF ULTRAPURE WATER

FIELD OF THE INVENTION

The invention relates to a method for analyzing the level of purity of a liquid obtained after purification treatment and in particular that of so-called ultrapure water (less than 10 parts per billion (ppb)). It also relates to a device capable of implementing that method.

BACKGROUND OF THE INVENTION

The method generally employed for purifying water, or any other liquid, begins with passage through a first device including filtration and purification means, of the type activated carbon filtering, ion exchange resin filtering or reverse osmosis filtering. At the outlet of the first treatment means, the ultrapure water contains very few ions and is characterized by a resistivity close to, or even equal to, 18.2 MΩ·cm, but still contains organic compounds. It is then passed through a second device in which those organic compounds are oxidized in order to ionize them. During this oxidation the organic compounds are degraded and the atoms of carbon are then present in the form of carbon dioxide gas, which is dissolved in water to form bicarbonate ions $HCO_3^-$. This oxidation is obtained by passage in front of an ultraviolet lamp or by adding hydrogen peroxide.

The third purification step consists in polishing the water, i.e. passing it through an ion exchange resin that blocks the ions created during the preceding step and thus completes the purification of the water. During this step the organic compounds that were not degraded during the oxidation phase are not affected.

It remains to determine the purity of the water obtained at the end of this process. One method commonly employed measures its resistivity at the outlet from the oxidation means, which is directly linked to the dissolved carbon dioxide gas content, i.e. to the number of bicarbonate ions, and then determines the resistivity that it would have if the oxidation process had been continued until the end, i.e. if all its organic compounds had been degraded. This process, necessitating an infinite time period, can obviously not be used and it is therefore necessary to employ methods of estimating this limit resistivity.

There is already known, in particular from the Millipore Corporation patent EP0581157, a device and a method for analyzing the purity of water that utilize the difference in the resistivity of the water between the upstream and downstream sides of the oxidation means to estimate this resistivity at infinity. This method uses the device in a first or reference mode to measure the resistivity difference between the upstream side and the downstream side of the oxidation means on water samples that have been exposed for various times to the oxidation means. The exposure times are typically of the order of 10, 20, 30, 40, 50 and 60 seconds. By extrapolation from the curve obtained, it is possible to determine what the resistivity of the water obtained would be after an infinite exposure time, i.e. if all the carbon atoms were to be degraded. Using an appropriate modeling program, such as the MINTEQA2 program described in the publication EPA/600/3-91/021 (1991) of the US Environmental Protection Agency, it is possible to determine from the resistivity at infinity the total organic carbon (TOC) content in the reference water.

A second or purification or analysis mode is then used during which ultrapure water is passed at a given flow rate through oxidation means to determine its content of organic compound impurities and thus to verify that its purity remains nominal. The resistivity difference between the upstream and downstream sides of the oxidation means is measured continuously and the total quantity of organic compounds is deduced therefrom by means of an assumed linear relationship between the resistivity difference measured in the purification mode and the resistivity difference at infinity estimated in the reference mode.

SUMMARY OF THE INVENTION

The invention aims to improve the method for measuring the purity of water used in the prior art.

To this end the method for the invention of analyzing the quantity of organic compound existing in a liquid, such as ultrapure water, at the outlet from a purification device including in series filter means, oxidation means and polishing means and further including means for measuring the resistivity of the water at the outlet of said filter means and at the outlet of said oxidation means, includes the following steps:

a) measuring the resistivity $\rho_{UPW}$ of the liquid at the outlet of the filter means;

b) establishing a reference mode by exposing a portion of the liquid to said oxidation means for a predetermined number of significantly different time periods and measuring the corresponding resistivity values of the liquid after its exposure to said oxidation means;

c) determining in this reference mode the resistivity at infinity $\rho_{\infty REF}$ of said liquid by establishing by regression a formula expressing its resistivity $\rho$ as a function of time t, said formula including at least one exponential function of the type $\rho = \rho_{\infty REF} + (\rho_{UPW} - \rho_{\infty REF})e^{-t/T}$;

d) establishing an analysis mode by passing said liquid to be analyzed through one of said resistivity measuring means to determine its resistivity $\rho$ at the outlet from the oxidation means;

e) determining the purity of the water from the measured resistivity $\rho$, the resistivity $\rho_{UPW}$ of the water at the outlet from the filter means and the resistivity at infinity $\rho_{\infty REF}$ estimated in the reference mode;

characterized in that said step e) of determining the purity includes the following sub-steps:

determining the time constant T of the exponential function established in the step c);

determining the resistivity at infinity p, of said liquid in this analysis mode by successive iterations until this parameter converges, expressing the measured resistivity $\rho$ as a function of this resistivity at infinity $\rho_\infty$ by a formula including at least one exponential function of the type $\rho = \rho_\infty + (\rho_{UPW} - \rho_\infty)e^{-t/T}$, t being an iteration variable, and by varying the iteration variable t toward infinity;

determining the quantity of organic compounds contained in said purified liquid from this resistivity at infinity $\rho_\infty$.

This method has the particular advantage of providing an approximation of the resistivity at infinity of the purified water that is much better than those given by the prior art and therefore provides a better indication of the instantaneous purity of the water. This better approximation of the resistivity value at infinity is obtained by calculating it by solving an equation based on a theoretical exponential relationship between the measured resistivity and that at infinity; the linear approximation used heretofore was valid only for limited purity differences between that of the water used in the reference mode and that of the water being tested. For example, if water with a purity of 3 ppb is used for the reference mode, the method would be applicable only for water with purity below 20 ppb.

According to features that are preferred for reasons of even better approximation of the resistivity at infinity or of simplification of the calculation, said formula used in the step c) is the sum of an exponential function of t and a linear function of t.

This feature makes the method usable with reactors of lower cost, including plastic material parts. The prior art reference mode presupposes that the evolution of the resistivity as a function of the time passed in the oxidation means is a purely exponential function. This simplification does not take account of contamination of the water by the plastics constituting the UV reactor of the oxidation means, which release organic compounds as a result of the photo-ionization to which they are subjected and those compounds are added to the compounds already present in the water. The proposed method takes this feature into account and means that there is no limitation to top of the range reactors produced in stainless steel, which are not subject to this unwanted kind of deterioration.

According to other features preferred for reasons of even better approximation of the resistivity at infinity or of simplification of the calculation:

- the number of different time periods used in the step b) is greater than or equal to six;
- said formula used in the step e) to express the resistivity at infinity in analysis mode is a formula including a single function of t of exponential form;
- the formula used in the step e) to express the resistivity at infinity in analysis mode is the sum of an exponential function of t and a linear function of t; and
- all the resistivity measurements are effected in the same resistivity measuring means.

The method uses only one resistivity measuring cell, with the aim of avoiding the uncertainty problems encountered if the calculation uses the value of the difference between a number of cells, and above all of reducing costs since, because of their complexity, these cells account for a large portion of the overall cost of the device.

The invention also relates to a device for analyzing the quantity of organic compounds existing in a liquid, such as ultrapure water, including in series filter means, oxidation means and polishing means, including means for measuring the resistivity of the water at the outlet from said filter means and at the outlet from said oxidation means, and further including:

- control means for exposing a portion of the liquid to said oxidation means during a determined number of significantly different time periods;
- means for determining by regression the resistivity at infinity $\rho_{\infty REF}$ of said liquid from the resistivities measured at the outlet from the oxidation means after said exposure time periods;

characterized in that it also includes

- means for determining, from the resistivities measured at the outlet from the oxidation means after said exposure time periods, the time constant T of the curve of evolution as a function of time of the resistivity $\rho$ at the outlet from the oxidation means, expressed by a formula including at least one exponential function of the type $\rho=\rho_{REF}+(\rho_{UPW}-\rho_{\infty REF})e^{-t/T}$, $\rho_{UPW}$ being the resistivity of the liquid measured at the outlet from the filter means;
- means for determining by successive iterations, until this parameter converges, the resistivity at infinity $\rho_\infty$ of the liquid at the outlet from the oxidation means, expressing the measured resistivity $\rho$ as a function of this resistivity at infinity $\rho_\infty$ by a formula including at least one exponential function of the type $\rho=\rho_\infty(\rho_{UPW}-\rho_\infty)e^{-t/T}$, t being an iteration variable, and causing the iteration variable t to vary toward infinity;
- means for determining the quantity of organic compounds contained in said purified liquid from this resistivity at infinity $\rho_\infty$; and
- means for displaying the result obtained.

BRIEF DESCRIPTION OF THE DRAWINGS

The disclosure of the invention continues next with the description of a preferred embodiment given hereinafter by way of nonlimiting illustration and with reference to the appended drawings. In the drawings.

DETAILED DESCRIPTION OF THE INVENTION

Figure 1:
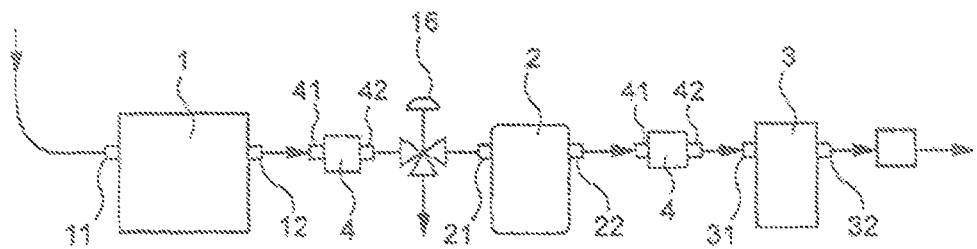
FIG. 1 is a diagram of a prior art water purification device.

FIG. 1 shows a prior art water purification device comprising, in series, filter means 1, oxidation means 2 and water polishing means 3. Two cells for measuring the resistivity of the water 4 are inserted into the circuit respectively at the outlet of the filter means 1 and at the outlet of the oxidation means 2.

The filter means 1 typically consist of filters based on activated carbon such as those marketed by the company Millipore Corporation under the trade mark Q-GARD®. At the outlet of these filter means the water has a purity of approximately 10 ppb and a resistivity close to or equal to 18.2 MΩ·cm.

Here the oxidation means 2 consist of a mercury vapor UV lamp radiating in the range from 185 to 254 nanometers. The water that flows through the purification device is exposed to this radiation for time periods from 2 to 120 seconds.

The polishing means 3 typically consist of an ion exchange resin and produce water with a final purity of the order of 1 to 5 ppb.

Water enters the device through the inlet point 11 of the filter means. The outlet point 12 of the filter means is connected by a pipe to the inlet point 41 of the first resistivity cell 4, the outlet of which is connected to a three-way valve 16. This three-way valve 16 is connected on the one hand to the inlet point 21 of the oxidation means and on the other hand to an evacuation circuit (not shown). It causes water leaving the filter means to enter the oxidation means 2 or evacuates it from the circuit.

The outlet point of the oxidation means 22 is connected by a pipe to the inlet point 41 of the second resistivity cell 4, the outlet point 42 of which is itself connected to the inlet point 31 of the polishing means. The ultrapure water obtained is then available at the outlet point 32 of the polishing means.

Figure 2:
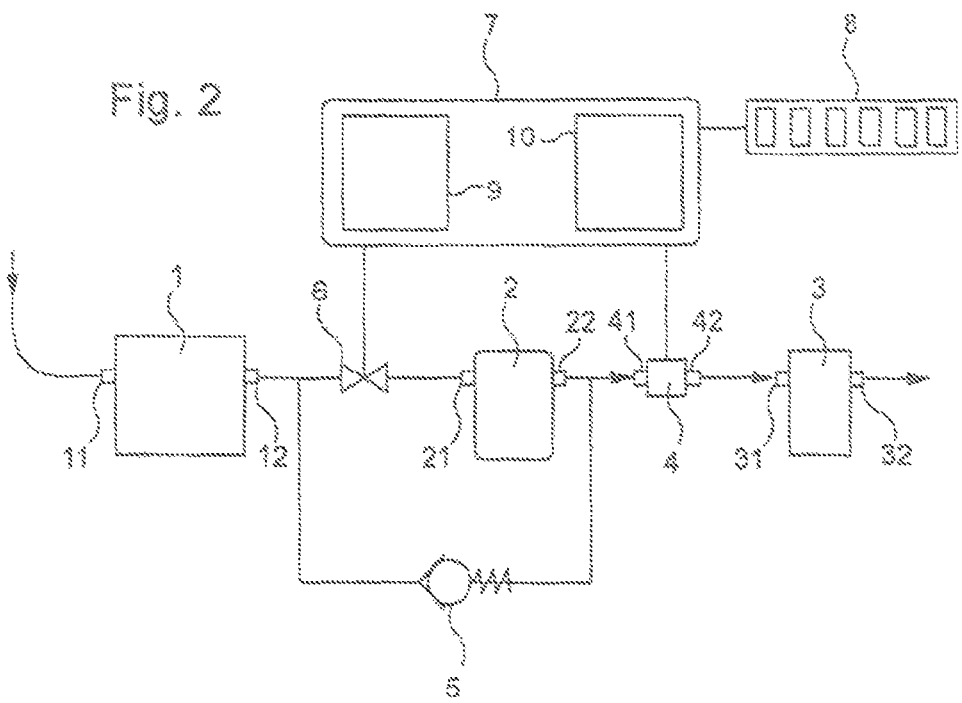
FIG. 2 is a diagram of a water purification device of one embodiment of the invention.

FIG. 2 shows a water purification device of one embodiment of the invention, comprising in series as above filter means 1, oxidation means 2 and water polishing means 3. This circuit differs from the prior art circuit in that it includes only one measuring cell 4, placed in series between the outlet point 22 of the oxidation means 2 and the inlet point 31 of the polishing means 3, and in that the three-way valve 16 is replaced by a simple analysis valve 6 with two positions, open and closed, that is less costly and easier to use.

Water at the outlet of the filter means is divided between two pipes, one of which goes to the analysis valve 6, as above, and a second of which, forming a bypass circuit, goes directly to the resistivity measuring cell 4 via a check valve 5 calibrated to open above a certain value.

Water from the filter means 1 is directed, entirely by action on the analysis valve 6, either to the oxidation means 2 or directly to the measuring cell 4 via the branch circuit equipped with the check valve 5. When the analysis valve 6 is in the open position, it allows liquid to pass to the oxidation means; the pressure in the branch circuit falls and the check valve 5 remains closed. If the analysis valve 6 is closed, the pressure rises in the branch circuit and the check valve 5 opens, allowing water to pass to the resistivity measuring cell 4.

FIG. 2 also shows control means for the water purification device, which include a control and calculation unit 7 and a display device 8 adapted to provide the operator in real time with information on the purity level obtained. This control and calculation unit 7 controls the position of the analysis valve 6 by means of a control module 9 and processes information supplied by the resistivity measuring cell 4 in a calculation module 10. The calculation module 10 executes the water purity calculation method and transmits the result obtained to the display device 8.

As in the prior art, the method for measuring the purity of water comprises a first measurement of the resistivity of the water at the outlet of the filter means followed by the use of two distinct operating modes of the purification device, a reference mode and an analysis mode. To evaluate the resistivity of the water supplied by the filter means 1, the analysis valve 6 is closed and the pressure on the upstream side of the check valve increases; the valve opens when the pressure reaches the nominal opening value and the flow of liquid circulates in the branch circuit via the check valve 5. In analysis mode or in reference mode, when the analysis valve is open, the check valve 5 prevents circulation of the liquid in the branch circuit, the pressure at its inlet remaining below the nominal opening pressure. The analysis valve is open continuously in analysis mode. In reference mode, however, it remains closed during predetermined time periods during which the water situated in the oxidation means continues to be exposed to the UV radiation. The analysis valve is then opened to send irradiated water to the measuring cell 4. Thanks to the significantly different time periods, the reference module determines the evolution of the resistivity of the water as a function of the time it has spent in the oxidation means.

The configuration with a check valve 5 and an analysis valve 6 means that a single measuring cell 4 can be used to measure the resistivity at the outlet of the filter means 1 and at the outlet of the oxidation means 2. This is reflected firstly in a major saving in the cost of producing the device and secondly by greater ease of use, the three-way valves of the prior art being complicated to use under the hydraulic operating conditions of the device.

Figure 3:
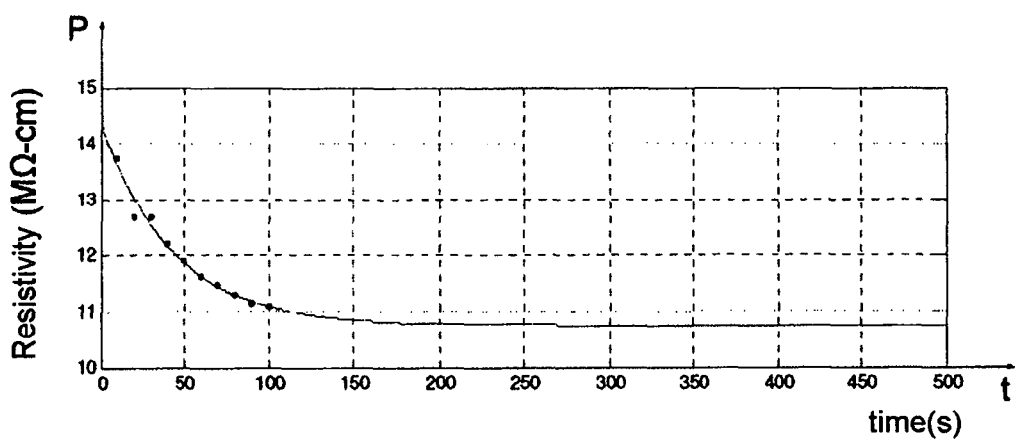
FIG. 3 is a curve representing the decrease of the resistivity of the water from any value, in the reference mode, as a function of the time spent in the reactor, using a prior art approximation method.
Figure 4:
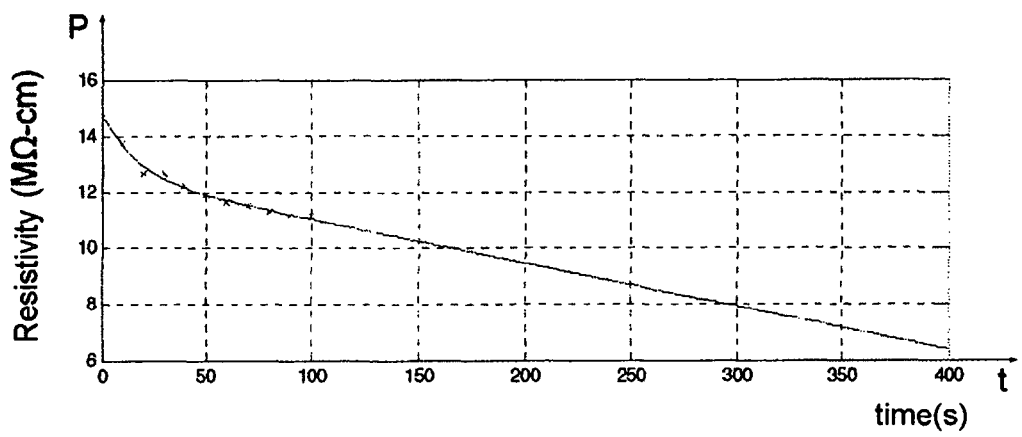
FIG. 4 is a curve representing the decrease of the resistivity of the water from any value, in the reference mode, as a function of the time spent in the reactor, using an approximation method for the invention.

FIG. 3 shows a number of points indicating the resistivity of the water at the outlet of the oxidation means 2 as a function of the time that it has spent in those means. FIG. 3 also gives a curve approximating those points by an exponential function of the type $\rho(t)=\rho_\infty+(\rho_0-\rho_\infty)e^{-t/T}$. FIG. 4 gives the resistivity value of the same points and an approximation curve produced by a mixed (exponential and linear) function, which can be represented as follows: $\rho(t)=\rho_\infty+(\rho_0-\rho_\infty)e^{-t/T}+(\rho_{slope}t+\rho_{intercept})\cdot u_{start,\ length}(t)$ where $\rho_{slope}$ and $\rho_{intercept}$ are the slope and the ordinate at the origin of a linear function and $u_{start,\ length}(t)$ is a function having the value 0 on a first portion of the abscissa axis corresponding to a purely exponential function and a value of 1 for the remainder of the abscissa axis where the function can be treated as the sum of an exponential function and a linear function.

The FIG. 4 curve is a better approximation of the evolution of the resistivity as a function of the UV irradiation time, especially if the UV reactor has plastic material parts that are in contact with the water and are subjected to this radiation. The linear part of the curve takes into account the presence in the water of organic compounds that are generated by the photo-ionization of these materials or by dissolving carbon dioxide gas from the atmosphere. This new approximation curve reduces by 50% the adjustment effected using the least squares method.

The process leading to measurement of the purity of the water obtained after it passes through the purification device is described next.

The first operation is to measure the resistivity of the water at the outlet of the filter means 1, by closing the analysis valve 6. The water then flows via the branch circuit and the check valve 5 directly into the resistivity measuring cell 4, which gives the value of the resistivity of the water at the outlet of the filter means 1. This value $\rho_{UPW}$ remains a priori constant throughout the purification operation as it depends only on characteristics of the liquid before purification.

Next a series of operations in a so-called reference mode begins. The aim of this mode is to determine the resistivity at infinity $\rho_{\infty REF}$ of water that will serve as a reference fluid for the remainder of the measurements. The analysis valve 6 is open briefly, for the time to replace water present in the oxidation means with new water coming from the filter means, after which this analysis valve 6 is closed. This valve remains closed for a particular first, time period and is then opened so that water retained in the oxidation means passes into the resistivity measuring cell 4; the resistivity value of this water is recorded and then the same operation is started again, varying the time spent by the water in the oxidation means. There is obtained in this way a series of measurements of resistivity as a function of time and regression techniques are used to deduce the best approximation curve passing through these points in a diagram giving the resistivity as a function of time. There is then obtained the resolution of the parameters of the function $\rho(t)=\rho_{\infty REF}+(\rho_0-\rho_{\infty REF})e^{-t/T}+(\rho_{slope}t+\rho_{intercept})\cdot u_{start,length}(t)$ which were unknown until now, i.e. the parameters $\rho_{\infty REF}$, $\rho_0$, T, $\rho_{slope}$, $\rho_{intercept}$ and the cut-off point of the function $u_{start,\ length}$. This function with six unknown parameters makes it necessary to carry out experiments with at least six different durations. This determines in particular the parameter $\rho_{\infty REF}$ which gives the value of the resistivity that the water would have if it had remained an infinite time in the oxidation means, in other words if all its organic components had been degraded into bicarbonate ions.

The knowledge of these two values (values $\rho_{UPW}$ of the resistivity at the outlet of the filter means and value $\rho_{\infty REF}$ of the resistivity at infinity after complete oxidation) provide for starting the phase of analyzing the water coming from the purification device and of knowing at all times its concentration in carbon atoms, i.e. its purity level. To this end the analysis valve is left open continuously.

Water that has passed through the filter means passes with a given flow rate through the oxidation means where it is subject to partial degradation of its organic components and where its resistivity evolves because of the dissolution of the carbon dioxide gas generated in this way. At the outlet of the oxidation means its resistivity ρ is measured by the measuring cell 4 and is a function of the residence time t during which it continued to be exposed to irradiation by the oxidation means 2.

Taking the single exponential curve for the resistivity evolution model, we can write $\rho(t)=\rho_\infty+(\rho_{UPW}-\rho_\infty)e^{-t/T}$. The approximation, applied here, which consists in retaining only the exponential part of the curve for the evolution of resistivity as a function of time and that could not have been taken into account in the reference mode with reactors including plastic material parts, is acceptable here because the exposure times of the water in the UV reactor remain short, which was not the case in the reference mode.

The value to be determined next is the value $\rho_\infty$ that is used to obtain the purity of the water at the outlet from the purification device. This parameter is calculated by an analytical extrapolation method explained below.

Designating by $k_\alpha$ the ratio between the terms $\rho(t)$ and $\rho_\infty$ and by $e^{-\alpha}$ the formula $e^{-t/T}$, for simplicity, we obtain:

$$1/k_\alpha = 1+(\rho_{UPW}/\rho_\infty - 1)e^{-\alpha}$$

By stating that this formula applies equally to the reference mode, in the left-hand portion of its curve ($u_{start,\,length}(t)=0$) for the same residence time, we obtain:

$$K_{REF}=\rho(t)_{REF}/\rho_{\infty REF}, \text{ and}$$

$$e^{-\alpha}=(1-K_{REF})/K_{REF}\times \rho_{\infty REF}(\rho_{UPW}-\rho_{\infty REF}).$$

It is then possible to express $k_\alpha$ as a function of $\rho_\infty$ and parameters that are known through using the reference mode ($K_{REF}$, $\rho_{UPW}$ and $\rho_{\infty REF}$).

Using the residence time t as a working parameter intended to tend toward infinity, it is possible, using a standard iterative method, to cause $k_\alpha$ and $\rho_\infty$ to evolve successively until the latter parameter converges.

There is obtained in this way the value of the resistivity that the water in the oxidation means would have if it had remained therein for an infinite time, i.e. if oxidation of its organic compounds had continued until complete.

Standard methods, for example that used by the MINTEQA2 program, then work back from the value of the resistivity at infinity to the total organic carbon (TOC) content of the water, i.e. its purity expressed in ppb.

In a variant of the method explained that retains only the exponential part of the resistivity evolution curve as a function of time it is obviously possible, in the analysis mode, to use the complete formula associating an exponential part and a linear part and to solve the corresponding equation.

Numerous other variants are possible as a function of circumstances, and in this regard it must be pointed out that the invention is not limited to the examples described and shown.

The invention claimed is:

1. Method for analyzing the quantity of organic compound existing in a liquid, at the outlet from a purification device including in series filter means, oxidation means and polishing means and further comprising means for measuring the resistivity of the water at the outlet of said filter means and at the outlet of said oxidation means, including the following steps:
    a) measuring the resistivity $\rho_{UPW}$ of the liquid at the outlet of the filter means (1);
    b) establishing a reference mode by exposing a portion of the liquid to said oxidation means for a predetermined number of significantly different time periods and measuring the corresponding resistivity values of the liquid after its exposure to said oxidation means;
    c) determining in this reference mode the resistivity at infinity $\rho_{\infty REF}$ of said liquid by establishing by regression a formula expressing its resistivity ρ as a function of time t, said formula including at least one exponential function of the type $\rho=\rho_{\infty REF}+(\rho_{UPW}-\rho_{\infty REF})e^{-t/T}$;
    d) establishing an analysis mode by passing said liquid to be analyzed through one of said resistivity measuring means to determine its resistivity ρ at the outlet from the oxidation means;
    e) determining the purity of the water from the measured resistivity ρ, the resistivity $\rho_{UPW}$ of the water at the outlet from the filter means and the resistivity at infinity $\rho_{\infty REF}$ estimated in the reference mode;
wherein said step e) of determining the purity includes the following sub-steps:
determining the time constant T of the exponential function established in the step c);
determining the resistivity at infinity $\rho_\infty$ of said liquid in this analysis mode by successive iterations until this parameter converges, expressing the measured resistivity ρ as a function of this resistivity at infinity $\rho_\infty$ by a formula including at least one exponential function of the type $\rho=\rho_\infty+(\rho_{UPW}-\rho_\infty)e^{-t/T}$, t being an iteration variable, and by varying the iteration variable t toward infinity; and
determining the quantity of organic compounds contained in said purified liquid from this resistivity at infinity $\rho_\infty$.

2. Analysis method according to claim 1 wherein the formula used in the step c) is the sum of an exponential function of t and a linear function of t.

3. Analysis method according to claim 2 wherein the number of different time periods used in the step b) is greater than or equal to six.

4. Analysis method according to any one of claims 1 to 3 wherein the formula used in the step e) to express the resistivity at infinity in analysis mode is a formula including a single function of t of exponential form.

5. Analysis method according to any one of claims 1 to 3 wherein the formula used in the step e) to express the resistivity at infinity in analysis mode is the sum of an exponential function of t and a linear function of t.

6. Analysis method according to any one of claims 1 to 3 wherein all the resistivity measurements are effected in the same resistivity measuring means.

7. Device for analyzing the quantity of organic compounds existing in a liquid, including in series filter means, oxidation means and polishing means, including means for measuring the resistivity of the water at the outlet from said filter means and at the outlet from said oxidation means, and further including:
    control means for exposing a portion of the liquid to said oxidation means during a determined number of significantly different time periods;
    means for determining by regression the resistivity at infinity $\rho_{\infty REF}$ of said liquid from the resistivities measured at the outlet from the oxidation means after said exposure time periods;
    wherein it also includes
    means for determining, from the resistivities measured at the outlet from the oxidation means after said exposure time periods, the time constant T of the curve of evolution as a function of time of the resistivity ρ at the outlet from the oxidation means, expressed by a formula including at least one exponential function of the type $\rho = \rho_{\infty REF} + (\rho_{UPW} - \rho_{\infty REF})e^{-t/T}$, being the resistivity of the liquid measured at the outlet from the filter means;

means for determining by successive iterations, until this parameter converges, the resistivity at infinity $\rho_\infty$, of the liquid at the outlet from the oxidation means, expressing the measured resistivity $\rho$ as a function of this resistivity at infinity $\rho_\infty$ by a formula including at least one exponential function of the type $\rho = \rho_\infty + (\rho_{UPW} - \rho_\infty)e^{-t/T}$, t being an iteration variable, and causing the iteration variable t to vary toward infinity;

means for determining the quantity of organic compounds contained in said purified liquid from this resistivity at infinity $\rho_\infty$;

and means for displaying the result obtained.

8. Analysis method according to claim 4 wherein all the resistivity measurements are effected in the same resistivity measuring means.

9. The method of claim 1, wherein said liquid is ultrapure water.

10. Method for analyzing the quantity of organic compound existing in a liquid, at the outlet from a purification device including in series, a filter, an oxidizer and a polisher, and further comprising a resistivity measuring cell for measuring the resistivity of the water at the outlet of said filter and at the outlet of said oxidizer, including the following steps:

a) measuring the resistivity $\rho_{UPW}$ of the liquid at the outlet of said filter;

b) establishing a reference mode by exposing a portion of the liquid to said oxidizer for a predetermined number of significantly different time periods and measuring the corresponding resistivity values of the liquid after its exposure to said oxidizer;

c) determining in this reference mode the resistivity at infinity $\rho_{\infty REF}$ of said liquid by establishing by regression a formula expressing its resistivity $\rho$ as a function of time t, said formula including at least one exponential function of the type $\rho = \rho_{\infty REF} + (\rho_{UPW} - \rho_{\infty REF})e^{-t/T}$;

d) establishing an analysis mode by passing said liquid to be analyzed through said resistivity measuring cell to determine its resistivity $\rho$ at the outlet from the oxidizer;

e) determining the purity of the water from the measured resistivity $\rho$, the resistivity $\rho_{UPW}$ of the water at the outlet from the filter and the resistivity at infinity $\rho_{\infty REF}$ estimated in the reference mode;

wherein said step e) of determining the purity includes the following sub-steps:

determining the time constant T of the exponential function established in the step c);

determining the resistivity at infinity $\rho_\infty$ of said liquid in this analysis mode by successive iterations until this parameter converges, expressing the measured resistivity $\rho$ as a function of this resistivity at infinity $\rho_\infty$ by a formula including at least one exponential function of the type $\rho = \rho_\infty + (\rho_{UPW} - \rho_\infty)e^{-t/T}$, t being an iteration variable, and by varying the iteration variable t toward infinity; and determining the quantity of organic compounds contained in said purified liquid from this resistivity at infinity $\rho_\infty$.

11. Analysis method according to claim 10, wherein the formula used in step c) is the sum of an exponential function of t and a linear function of t.

12. Analysis method according to claim 11 wherein the number of different time periods used in the step b) is greater than or equal to six.

13. Analysis method according to claim 10, wherein the formula used in step e) to express the resistivity at infinity in analysis mode is a formula including a single function of t of exponential form.

14. Analysis method according to claim 10, wherein the formula used in step e) to express the resistivity at infinity in analysis mode is the sum of an exponential function of t and a linear function of t.

15. Analysis method according to claim 10, wherein all the resistivity measurements are effected in the same resistivity measuring cell.

* * * * *